U S009463486B2

(12) United States Patent
Wilkerson et al.

(10) Patent No.: US 9,463,486 B2
(45) Date of Patent: Oct. 11, 2016

(54) LAMINAR FLOW DROPLET GENERATOR DEVICE AND METHODS OF USE

(71) Applicant: Eyenovia, Inc., Tampa, FL (US)

(72) Inventors: Jonathan Ryan Wilkerson, Raleigh, NC (US); Iyam Lynch, Boone, NC (US); Louis Thomas Germinario, Kingsport, TN (US); Charles Eric Hunter, Boone, NC (US)

(73) Assignee: Eyenovia, Inc., Tampa, FL (US)

( * ) Notice: Subject to any disclaimer, the term of this patent is extended or adjusted under 35 U.S.C. 154(b) by 391 days.

(21) Appl. No.: 13/893,776

(22) Filed: May 14, 2013

(65) Prior Publication Data

US 2013/0334335 A1 Dec. 19, 2013

Related U.S. Application Data

(60) Provisional application No. 61/646,721, filed on May 14, 2012, provisional application No. 61/722,600, filed on Nov. 5, 2012.

(51) Int. Cl.
*B05B 1/08* (2006.01)
*B05B 17/00* (2006.01)
(Continued)

(52) U.S. Cl.
CPC .............. *B05B 17/0646* (2013.01); *B05B 1/02* (2013.01); *B05B 1/14* (2013.01); *B05B 1/28* (2013.01);
(Continued)

(58) Field of Classification Search
CPC ..... B05B 17/06; B05B 17/067; B05B 15/02; B05B 1/28; B05B 7/0012; B05B 1/14; B05B 1/02; B05B 17/0646; B05B 17/0661; B05B 17/0669; F02M 61/1853; A61F 9/0008; A61M 15/0085; A61M 15/0065; B06B 1/0651
USPC ......... 239/102.1, 102.2, 338, 552, 104, 120, 239/596, 601; 128/200.14, 200.16; 604/298
See application file for complete search history.

(56) References Cited

U.S. PATENT DOCUMENTS

| 4,533,082 A | 8/1985 | Maehara et al. |
| 5,024,355 A | 6/1991 | Jouillat et al. |

(Continued)

FOREIGN PATENT DOCUMENTS

| CN | 1854503 | 11/2006 |
| CN | 101479046 | 7/2009 |

(Continued)

OTHER PUBLICATIONS

Santvliet et al., "Determinants of Eye Drop Size," *Survey of Ophthamology*, Mar.-Apr. 2004, vol. 49, pp. 197-211.

(Continued)

*Primary Examiner* — Steven J Ganey
(74) *Attorney, Agent, or Firm* — Polsinelli PC

(57) ABSTRACT

A piezoelectric ejector device is provided which is designed to minimize the intake of air into the device upon actuation by providing for laminar flow of the fluid. In an ejector mechanism that includes a generator plate and a piezoelectric actuator operable to directly or indirectly oscillate the generator plate, at a frequency to generate a directed stream of droplets of fluid, the generator plate includes a fluid facing surface, a droplet ejection surface, and a plurality of holes formed through its thickness between the surfaces. The plurality of holes are configured so as to minimize airflow through the plurality of openings from the droplet ejection surface to the fluid facing surface during generation of the directed stream of droplets by configuring the shape of the holes to minimize turbulence.

12 Claims, 13 Drawing Sheets

(51) Int. Cl.
*B05B 1/28* (2006.01)
*B05B 17/06* (2006.01)
*B05B 7/00* (2006.01)
*B05B 15/02* (2006.01)
*B05B 1/14* (2006.01)
*B05B 1/02* (2006.01)
*B06B 1/06* (2006.01)
*F02M 61/18* (2006.01)
*A61M 15/00* (2006.01)
*A61F 9/00* (2006.01)

(52) U.S. Cl.
CPC ............ *B05B 7/0012* (2013.01); *B05B 15/02* (2013.01); *B05B 17/06* (2013.01); *B05B 17/0607* (2013.01); *B06B 1/0651* (2013.01); *A61F 9/0008* (2013.01); *A61M 15/0065* (2013.01); *A61M 15/0085* (2013.01); *B05B 17/0661* (2013.01); *B05B 17/0669* (2013.01); *F02M 61/1853* (2013.01)

(56) References Cited

U.S. PATENT DOCUMENTS

| | | | |
|---|---|---|---|
| 5,518,179 A * | 5/1996 | Humberstone | B05B 17/0646 239/102.2 |
| 5,607,410 A | 3/1997 | Branch | |
| 5,630,793 A | 5/1997 | Rowe | |
| 6,011,062 A | 1/2000 | Schneider et al. | |
| 6,550,472 B2 | 4/2003 | Litherland et al. | |
| 6,976,639 B2 | 12/2005 | Williams et al. | |
| 7,448,559 B2 | 11/2008 | Le Maner et al. | |
| 7,828,232 B2 * | 11/2010 | Oomori | F02M 51/061 239/104 |
| 7,883,031 B2 | 2/2011 | Collins, Jr. et al. | |
| 7,954,486 B2 | 6/2011 | Papania et al. | |
| 8,012,136 B2 | 9/2011 | Collins, Jr. et al. | |
| 8,545,463 B2 | 10/2013 | Collins, Jr. et al. | |
| 8,684,980 B2 | 4/2014 | Hunter et al. | |
| 2002/0085067 A1 | 7/2002 | Palifka et al. | |
| 2003/0116642 A1 * | 6/2003 | Williams | B41J 2/14008 239/102.1 |
| 2004/0039355 A1 | 2/2004 | Gonzalez et al. | |
| 2004/0215157 A1 | 10/2004 | Peclat et al. | |
| 2004/0256487 A1 | 12/2004 | Collins, Jr. et al. | |
| 2005/0211797 A1 | 9/2005 | Abergel et al. | |
| 2006/0011737 A1 * | 1/2006 | Amenos | A01M 1/2033 239/102.1 |
| 2007/0211212 A1 | 9/2007 | Bennwik | |
| 2008/0303850 A1 | 12/2008 | Shin et al. | |
| 2009/0114742 A1 | 5/2009 | Collins, Jr. | |
| 2009/0149829 A1 | 6/2009 | Collins, Jr. | |
| 2009/0167812 A1 | 7/2009 | Asai et al. | |
| 2009/0212133 A1 | 8/2009 | Collins, Jr. | |
| 2009/0272818 A1 | 11/2009 | Valpey et al. | |
| 2010/0211408 A1 | 8/2010 | Park et al. | |
| 2010/0222752 A1 | 9/2010 | Collins, Jr. et al. | |
| 2011/0175971 A1 | 7/2011 | Newton et al. | |
| 2011/0233302 A1 | 9/2011 | Lin et al. | |
| 2011/0254901 A1 | 10/2011 | Sakai | |
| 2012/0062840 A1 | 3/2012 | Ballou, Jr. et al. | |
| 2012/0070467 A1 | 3/2012 | Ballou, Jr. et al. | |
| 2012/0143152 A1 | 6/2012 | Hunter et al. | |
| 2013/0150812 A1 | 6/2013 | Hunter et al. | |
| 2013/0172830 A1 | 7/2013 | Hunter et al. | |
| 2013/0299607 A1 | 11/2013 | Wilkerson et al. | |
| 2014/0336618 A1 | 11/2014 | Wilkerson et al. | |
| 2014/0361095 A1 | 12/2014 | Haran | |

FOREIGN PATENT DOCUMENTS

| | | |
|---|---|---|
| EP | 1219314 | 7/2002 |
| EP | 2253322 | 11/2010 |
| FR | 2934128 | 1/2010 |
| WO | WO 95/15822 | 6/1995 |
| WO | WO 2011/083379 | 7/2011 |
| WO | WO 2012/009696 | 1/2012 |
| WO | WO 2012/009706 | 1/2012 |
| WO | WO 2012/119702 | 1/2012 |
| WO | WO 2013/090468 | 6/2013 |

OTHER PUBLICATIONS

Brown et al., "The Preservation of Ophthalmic Preparations," *Journal of the Society of Cosmetic Chemists*, 1965, vol. 16, pp. 369-393.

* cited by examiner 4-hole with mesa 21-hole 37-hole

LAMINAR FLOW DROPLET GENERATOR DEVICE AND METHODS OF USE

RELATED APPLICATIONS

The present application claims the benefit of the filing date of U.S. Patent Application Nos. 61/646,721, filed May 14, 2012, entitled "Ejector Mechanism, Ejector Device and Methods of Use" and 61/722,600 filed Nov. 5, 2012, entitled "Laminar Flow Droplet Generator Device and Methods of Use", the contents of which are herein incorporated by reference in their entireties.

BACKGROUND OF THE INVENTION

Using spray devices to administer products in the form of mists or sprays is an area with large potential for safe, easy-to-use products. An important area where spray devices are needed is in delivery of eye medications. However, a major challenge in providing such a device is to provide consistent and accurate delivery of suitable doses. In addition, a multi-dose spray device may become exposed to possible contamination as a result of interaction with a non-sterile outside environment.

Accordingly, there is a need for a delivery device that delivers safe, suitable, and repeatable dosages to a subject for ophthalmic, topical, oral, nasal, or pulmonary use.

SUMMARY OF THE INVENTION

The present disclosure relates, in part, to an ejector mechanism, ejector device and method of delivering safe, suitable, and repeatable dosages to a subject for ophthalmic, topical, oral, nasal, or pulmonary use. The present disclosure relates to an ejector device and fluid delivery system capable of delivering a defined volume of the fluid in the form of a directed stream of droplets having properties that afford adequate and repeatable high percentage deposition of droplets upon application.

According to the disclosure, a piezoelectric ejector device is provided which is designed to minimize the intake of air into the device upon actuation, as explained in further detail herein. The ejector mechanism may include a generator plate and a piezoelectric actuator operable to directly or indirectly oscillate the generator plate, at a frequency to generate a directed stream of droplets of fluid. The generator plate includes a fluid facing surface, a droplet ejection surface, and a plurality of openings formed through its thickness between the surfaces. According to the disclosure, the generator plate and its plurality of openings are configured so as to minimize airflow through the plurality of openings from the droplet ejection surface to the fluid facing surface during oscillation by promoting laminar flow of liquid as it passes from the fluid facing surface to the droplet ejection surface.

DETAILED DESCRIPTION

Figure 1:
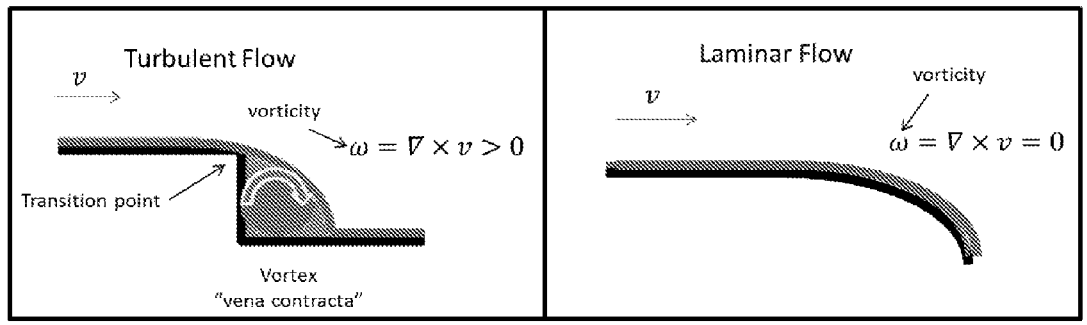
FIG. 1 shows illustrative turbulent and laminar flow, in accordance with aspects of the disclosure.
Figure 2:
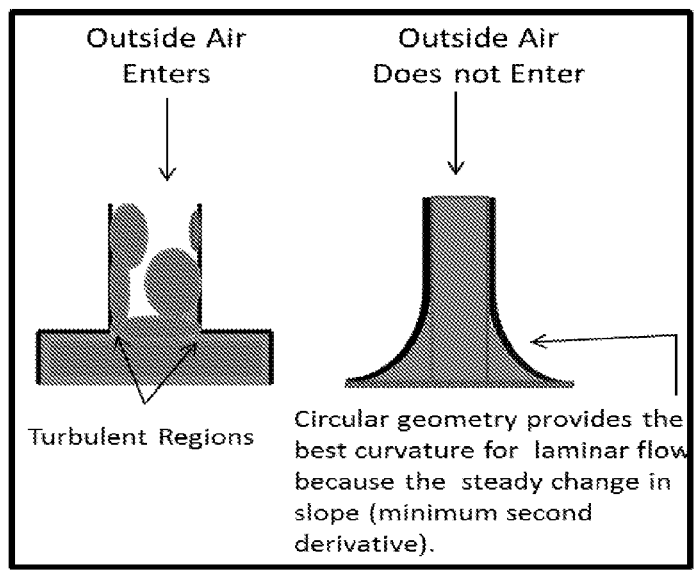
FIG. 2 shows exemplary generator plate opening geometries, resulting in turbulent flow (left) and laminar flow (right), in accordance with aspects of the disclosure.
Figure 3:
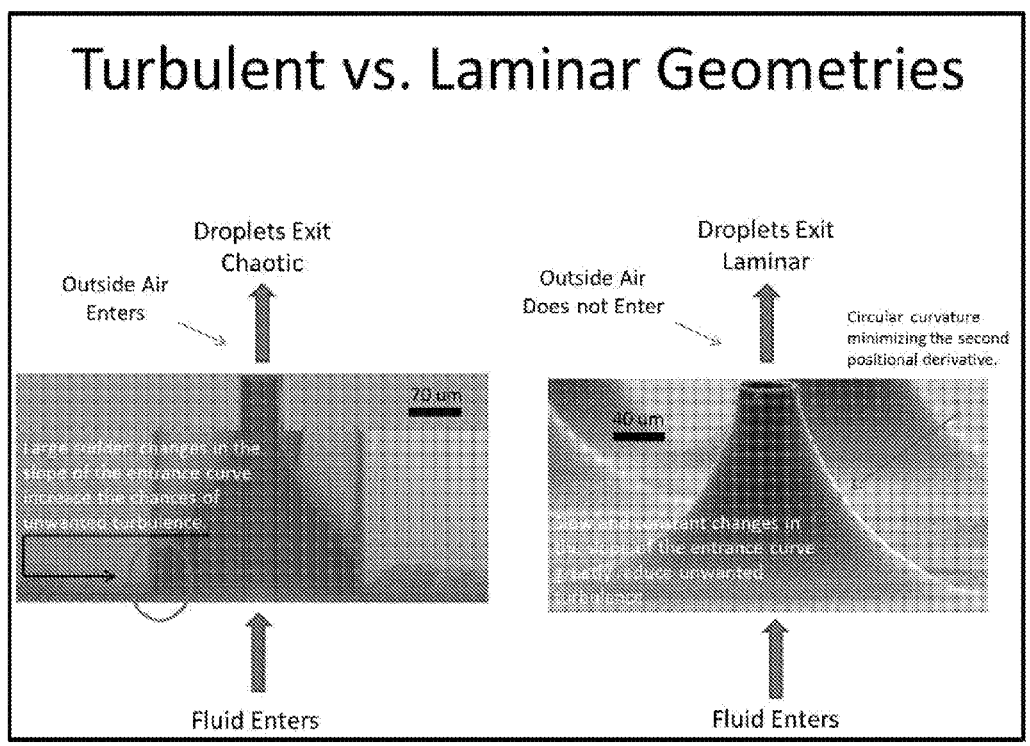
FIG. 3 shows exemplary generator plate opening geometries, resulting in turbulent flow (left) and laminar flow (right), in accordance with aspects of the disclosure.
Figure 4:
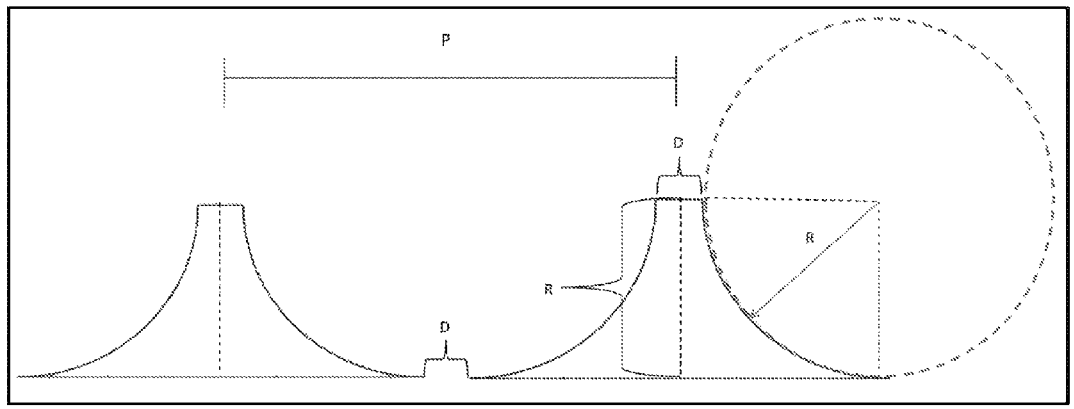
FIG. 4 illustrates exemplary curvatures of laminar flow generator plate openings, in accordance with aspects of the disclosure.
Figure 5:
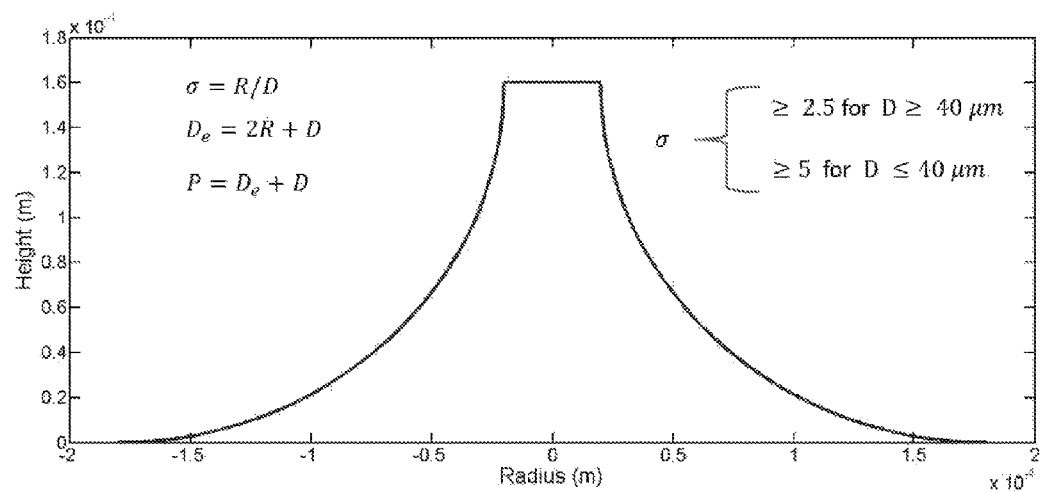
FIG. 5 illustrates exemplary curvatures of laminar flow generator plate openings, in accordance with aspects of the disclosure.
Figure 6:
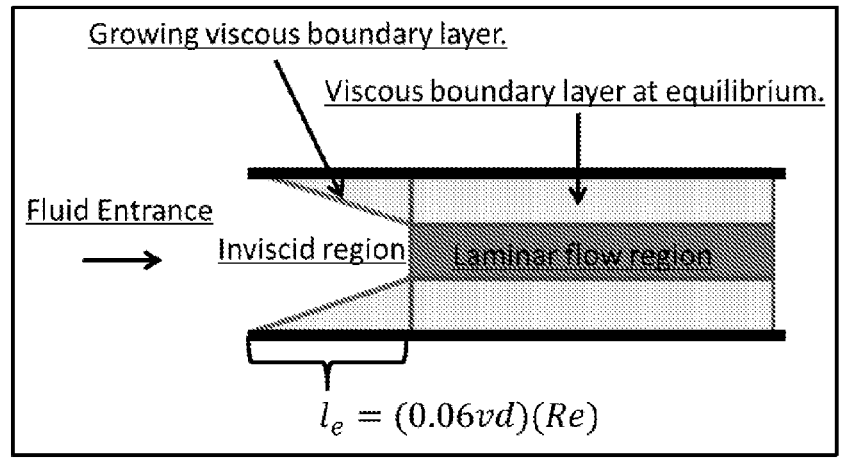
FIG. 6 illustrates entrance length parameters of a pipe/opening, in accordance with embodiments of the disclosure.

The present disclosure generally relates to piezoelectric ejector devices useful, e.g., in the delivery of fluids, such as ophthalmic fluids to the eye. The ejector device may include an ejector assembly including an ejector mechanism and a fluid supply. In certain aspects, the ejector mechanism may comprise a piezoelectric actuator and a droplet generator plate, which are operable to generate a directed stream of droplets of fluid when the actuator is actuated to directly or indirectly oscillate the generator plate. Fluid includes without limitation, suspensions or emulsions which have viscosities in a range capable of droplet formation using an ejector mechanism.

Piezoelectric droplet generation and flow in micro-channels depends on a complex interaction between liquid flow through micro-orifices, fluid-surface interactions, exit orifice diameter, entrant cavity geometry, capillary tube length, ejector material mechanical properties, amplitude and phase of the mechanical displacement, and frequency of displacement of ejector plate. Moreover, fluid properties such as viscosity, density and surface energy play major roles in droplet formation. In accordance with certain aspects of the disclosure, novel ejector hole structures and geometries that optimize droplet generation dynamics and microfluidic flow have been developed. For example, certain embodiments related to computer controlled laser micromachining that provides accurate control of the three-dimensional topography of the ejector surface and nozzle geometry. This provides independent control over fluid velocity amplification, resistance, turbulence and valving of high viscosity fluids.

According to the present disclosure, a piezoelectric ejector device is provided which is designed to minimize the intake of air into the device upon actuation, as explained in further detail herein. As discussed above, the ejector mechanism includes a generator plate and a piezoelectric actuator operable to directly or indirectly oscillate the generator plate, at a frequency to generate a directed stream of droplets of fluid. The generator plate includes a fluid facing surface, a droplet ejection surface, and a plurality of openings formed through its thickness between the surfaces. As described in the various embodiments disclosed in the present disclosure, the generator plate and its plurality of openings are configured so as to minimize airflow through the plurality of openings from the droplet ejection surface to the fluid facing surface during generation of the directed stream of droplets. As explained herein, minimizing of airflow results, in part, in laminar flow of the directed stream of droplets. By way of background, but without intending to be limited by theory, intake of air into the ejector device during operation can result in unpredictable behavior within the device that may not only alter the operation of the device but in many cases may result in failure. Again, without being limiting, the vibrating pump-like action of the ejection area of the ejector mechanism of the disclosure creates pressure gradients that are both in the direction of droplet ejection as well as in the opposite direction of ejection. When the pressure gradient is aligned opposite to the direction of ejection, air within the surrounding region has an opportunity to move into the lower pressure area behind the active area by passing though the ejector openings.

However, the intake of air through the ejector openings may be prevented by the presence of fluid behind the ejector openings, thereby blocking the air from entering the system. In certain instances, air may enter the system through paths formed from gaps created during processes that interfere with proper symmetric fill conditions. These processes create chaotic turbulent regions between the liquid and air, which allow overpressures to occur that encapsulate the air that has moved into the openings to create bubbles.

One way in which air can enter the system by overcoming the resistance of generator plate openings is by fluid turbulence on the fluid side of the ejector mechanism created from an abrupt transition in fluid flow, for example, as fluid enters the fluid reservoir side of the generator plate. Rapidly moving fluid experiences a sudden change in flow due to a large and sudden change in slope at a transition point. With reference to FIG. 1A, the fluid "overshoots" the transition point region and shears the fluid below resulting in vortices or "vena contracta" which are regions of nonzero vorticity. As shown in FIG. 1A, this results in a vorticity $\omega$ (which is a function of fluid velocity) to have a value greater than 0. In contrast, when the transition is gradual, as shown in FIG. 1B, the shearing does not take place and vortices are avoided (vorticity $\omega=0$).

With reference to FIG. 2, the generator plate on the left shows an abrupt transition, resulting in turbulent flow and a chaotic spray, which allows outside air to enter into the system via the generator plate openings during operation. The illustrated generator plate opening comprises a shape with a large transition from fluid reservoir side to the droplet ejection side, which encourages the formation of vortices leading to broken flow and the formation of gaps within the opening. In contrast, the generator plate opening on the right has a gradual change in slope from the fluid reservoir side to the droplet ejection side, resulting in laminar flow and efficient spray.

The present disclosure generally relates to ejector devices useful, e.g., in the delivery of fluid for ophthalmic, topical, oral, nasal, or pulmonary use, more particularly, for use in the delivery of ophthalmic fluid to the eye. In one embodiment, the ejector device includes an ejector assembly including an ejector mechanism which generates a controllable stream of droplets of fluid. The ejector mechanism may be a charge isolated mechanism. Fluid includes, without limitation, suspensions or emulsions which have viscosities in a range capable of droplet formation using an ejector mechanism. Fluids may include pharmaceutical and medicament products.

As explained in further detail herein, the ejector mechanism may form a directed stream of droplets, which may be directed toward a target. The droplets may be formed in a distribution of sizes, each distribution having an average droplet size. The average droplet size may be in the range of about 15 microns to over 400 microns, greater than 20 microns to about 400 microns, about 20 microns to about 80 microns, about 25 microns to about 75 microns, about 30 microns to about 60 microns, about 35 microns to about 55 microns, about 20 microns to about 200 microns, about 100 microns to about 200 microns, etc. However, the average droplet size may be as large as 2500 microns, depending on the intended application. Further, the droplets may have an average initial velocity of about 0.5 m/s to about 100 m/s, e.g., about 0.5 m/s to about 20, e.g., 0.5 to 10 m/s, about 1 m/s to about 5 m/s, about 1 m/s to about 4 m/s, about 2 m/s, etc. As used herein, the ejecting size and the initial velocity are the size and initial velocity of the droplets when the droplets leave the ejector plate. The stream of droplets directed at a target will result in deposition of a percentage of the mass of the droplets including their composition onto the target.

As described herein, the ejector device and ejector mechanism of the disclosure may be configured to eject a fluid of generally low to relatively high viscosity as a stream of droplets. By way of example, fluids suitable for use by the ejector device can have very low viscosities, e.g., as with water at 1 cP, or less, e.g. 0.3 cP. The fluid may additionally have viscosities in ranges up to 600 cP. More particularly, the fluid may have a viscosity range of about 0.3 to 100 cP, 0.3 to 50 cP, 0.3 to 30 cP, 1 cP to 53 cP, etc. In some implementations, the ejection device may be used to eject a fluid having a relatively high viscosity as a stream of droplets, e.g., a fluid having a viscosity above 1 cP, ranging from about 1 cP to about 600 cP, about 1 cP to about 200 cP, about 1 cP to about 100 cP, about 10 cP to about 100 cP, etc. In some implementations, solutions or medications having a suitable viscosity and surface tensions can be directly used in the reservoir without modification. In other implementations, additional materials may be added to adjust the fluid parameter.

Droplets may be formed by an ejector mechanism from fluid contained in a reservoir coupled to the charge isolated ejector mechanism. The charge isolated ejector mechanism and reservoir may be disposable or reusable, and the components may be packaged in a housing of an ejector device, such as those described in U.S. Provisional Application Nos. 61/569,739, 61/636,559, 61/636,565, 61/636,568, 61/642,838, 61/642,867, 61/643,150 and 61/584,060, and in U.S. patent application Ser. Nos. 13/184,446, 13/184,468 and 13/184,484, the contents of which are incorporated herein by reference. More particularly, exemplary ejector devices and ejector mechanism are illustrated in U.S. Application No. 61/569,739, filed Dec. 12, 2011. entitled "Ejector Mechanism, Ejector Device, and Methods of Use," U.S. Application No. 61/636,565, filed Apr. 20, 2012, entitled "Centro-Symmetric Lead Free Ejector Mechanism, Ejector Device, and Methods of Use" and U.S. Application No. 61/591,786, filed Jan. 27, 2012, entitled "High Modulus Polymeric Ejector Mechanism, Ejector Device, And Methods Of Use," each of which are herein incorporated by reference in their entirety.

In accordance with certain embodiments of the disclosure, the openings of a generator plate of the disclosure are configured to have a shape with a gradual slope of change from the fluid facing surface to the droplet ejection surface. By way of background, without intending to be limited by theory, for fluid traveling in one dimension, the optimal function is linear (e.g., a pipe) and turbulence in the system is related to the Reynolds number, which is a function of the velocity, pipe diameter, density of fluid, and the viscosity of the fluid. The Reynolds number is a ratio of between inertial and viscous forces and is thus a dimensionless quantity. The flow is generally considered to be laminar when the Reynolds number is less than 2300 and is considered turbulent for values above 4000. In the region between 2300 and 4000 the flow is considered to be "transitional" which means that both laminar and turbulent flows are possible.

$$\mathrm{Re} = \frac{\rho v L}{\eta}$$

Where Re is the Reynolds number,
ρ is the density of the fluid,
v is the velocity of the fluid,
L is the pipe diameter, and
η is the viscosity of the liquid.

To minimize the presence of turbulent regions formed from quick transitions (steps) in the shape of an opening, the curvature may be a function with a small second derivative. In accordance with one aspect of the disclosure, the second order curve which provides a minimum value for the second derivative is the shape of a circle whose function is shown below. In this regard, such curvatures comprise a shape having an external entry radius of curvature having a circular shape from the fluid facing surface to the droplet ejection surface.

$$\frac{d^2 y}{d x^2} = \frac{R^2}{(R^2 - x^2)^{\frac{3}{2}}}$$

Where R is the external radius of the curve.

With reference to FIG. 3, an opening having an external entry curvature that is not circular in shape is illustrated on the left. Such an opening exhibits a large sudden charge in the slope of the entrance curve thereby promoting turbulent flow and chaotic spray, which increases the ability of outside air to enter the system. In contrast, on the right an opening in accordance with one embodiment of the disclosure is illustrated, wherein the external entry radius of curvature comprises a circular shape, which results in laminar flow and minimizes the ability of outside air to enter the system.

Thus, laminar flow openings in accordance with the present disclosure may be configured with gradually changing circular curvature, which encourages laminar flow by minimizing voracity and eliminating the presence of vortices. With reference to FIGS. 4 and 5, dimensions for constructing laminar flow generator plate openings are provided in accordance with aspects of the disclosure. In FIG. 4, the variables P, R, and D represent the pitch between openings, radius of curvature of the circular entry shape, and exit diameter of the opening, respectively. In FIG. 5, the additional variables De and σ are the entrance diameter, and the ratio of radius of curvature to exit diameter, respectively.

In accordance with one aspect of the disclosure, the ratio σ (ratio of size of the radius of curvature to the size of the opening at the droplet ejection surface) defines the proper conditions for constructing laminar ejectors. In one embodiment, when the opening at the droplet ejection surface is greater than about 40 μm a σ was chosen to be equal to or greater than about 2.5. In another embodiment, the ratio σ of size of the radius of curvature to the size of the opening at the droplet ejection surface was chosen to be greater than about 5, when the opening at the droplet ejection surface was less than about 40 μm. It should be noted that the height or thickness of the mesh (defined by the generator plate) is not necessarily limited to the dimensions illustrated in FIG. 5 and can be larger or smaller than the dimensions shown.

According to another aspect, generator plate openings are configured so as to have an entrance length or generator plate thickness which facilitates the creation of a laminar flow region. By way of background, but without intending to be limited by theory, fluid entering a pipe (i.e., in the context of the present disclosure, fluid entering the opening of a generator plate) undergoes a period (length) in which laminar flow is not possible due to the initial boundary conditions between the fluid and the surface of the pipe/opening. This is illustrated in FIG. 6. At the boundary, entry wall friction and viscous forces dominate for the fluid closest to the surface. Under "no-slip" boundary conditions, the fluid immediately at the wall has a tangential velocity of zero, and this bound layer exerts a viscous drag on the neighboring fluid layers, which drag force decreases with distance away from the boundary layer. This causes layer dependent velocity regions to form in the fluid resulting in a non-uniform buildup of the final viscous boundary layer at equilibrium. The distance it takes for the boundary layer to build up to constant layer is what is known as the "entrance length". The "inviscid" region is the area where the effect of viscosity is negligible. Once the flow has gone past the entrance length $l_e$, laminar flow is possible (the laminar flow region is the region where Poiseuille flow is established). Poiseuille flow is a flow condition in which the velocity profile is parabolic. This distance $l_e$ is a function of the Reynolds number Re and is given by the expression $l_e=(0.06vd)(\mathrm{Re})$ where v, d, and Re are the velocity of the fluid, diameter of the nozzle and Reynolds number, respectively. The range of laminar flow as a function of Reynolds number applies for fluid that has moved past this initial entrance length $l_e$. In the chart below the values for both Reynolds number and entrance length were calculated assuming a velocity of 2 m/s which was chosen based on the average droplet speed values calculated in one embodiment and as provided by digital holographic microscopy (DHM) results for the embodiment, which measured the velocity for the active membrane within the range between 0.5-5 m/s. The ejector diameter hole size chosen for the chart was 40 microns. Surface tension values were measured with a goniometer (contact angle analyzer), viscosity measurements were performed on a tuning fork "vibro" viscometer, and density measurements were performed by measuring a known quantity of drug and weighing it using a sensitive scale.

The results are shown in Table 1 below:

| Drug | Surface Tension (mN/m) | Dynamic Viscosity (cP) | Density (g/mL) | Re | le (microns) |
|---|---|---|---|---|---|
| Saline | 72.3 | 1.015 | 0.984 | 80 | 192 |
| Latanoprost | 28.4 | 1.088 | 0.9827 | 85.6 | 205 |
| Restasis | 40.7 | 17.48 | 0.949 | 4.4 | 11 |
| Timolol | 37.6 | 1.23 | 0.975 | 63.4 | 152 |
| Tropicamide | 37.8 | 1.18 | 0.991 | 67.19 | 161 |
| Water | 72.8 | 1 | 0.9982 | 79.84 | 192 |

As was discussed above, the Reynolds number is a ratio between inertial and viscous forces and flow is generally considered to be laminar when the Reynolds number is less than 2300 and is considered turbulent for values above 4000. In the region between 2300 and 4000 the flow is considered to be "transitional" which means that both laminar and turbulent flows are possible. However, as is demonstrated by the results in Table 1 and as shown in FIG. 7 below, the Reynolds number is also related to the entrance length $l_e$.

Figure 7:
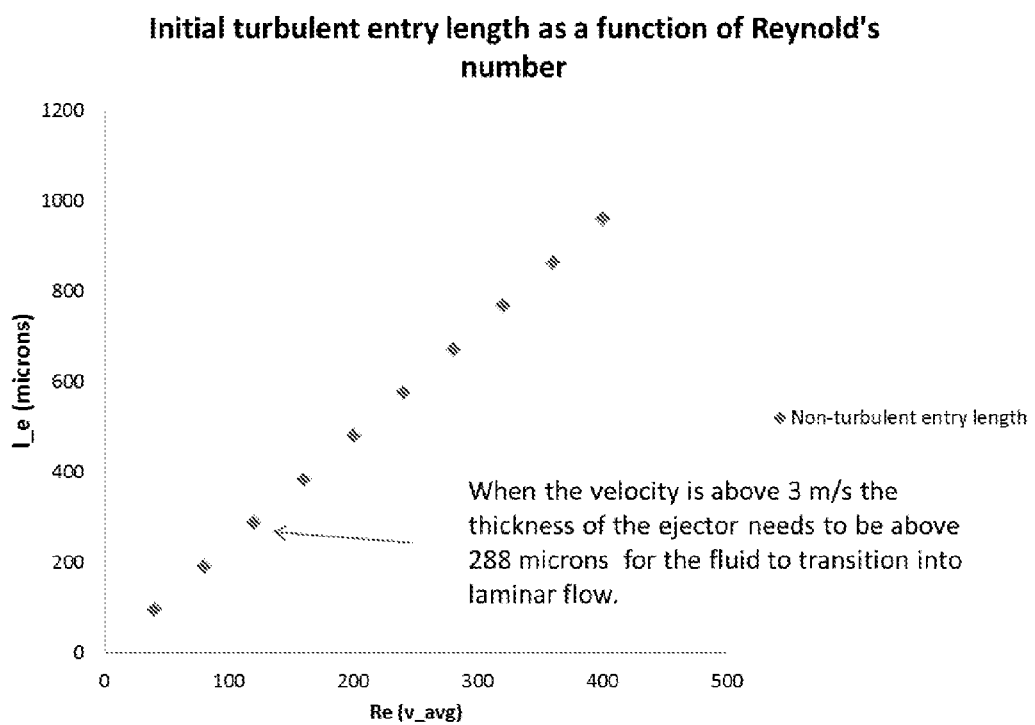
FIG. 7 shows a plot of initial turbulent entry length as a function of Reynold's number, in accordance with aspects of the disclosure.
Figure 8:
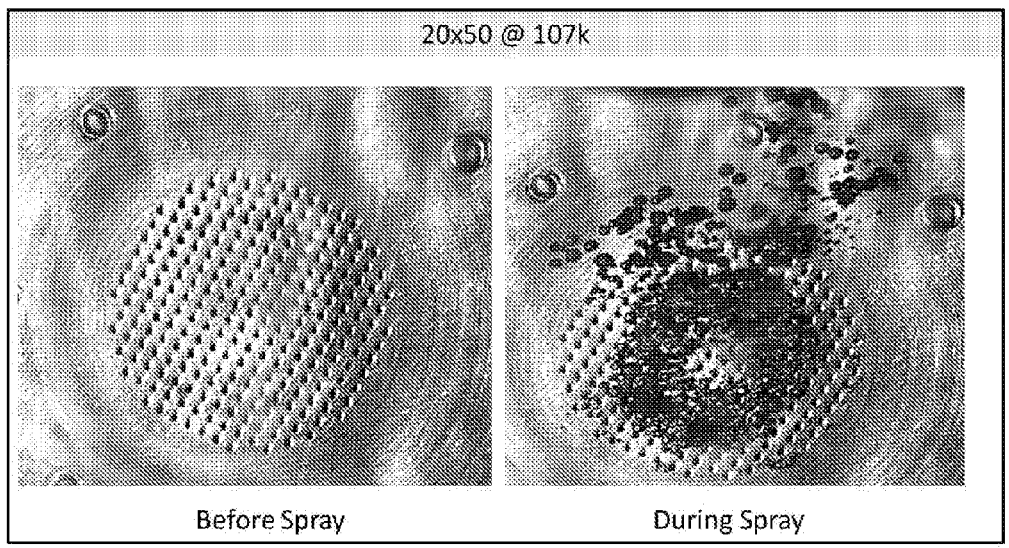
FIG. 8 illustrates one embodiment of a non-laminar NiCo ejector in operation according to the disclosure.
Figure 9:
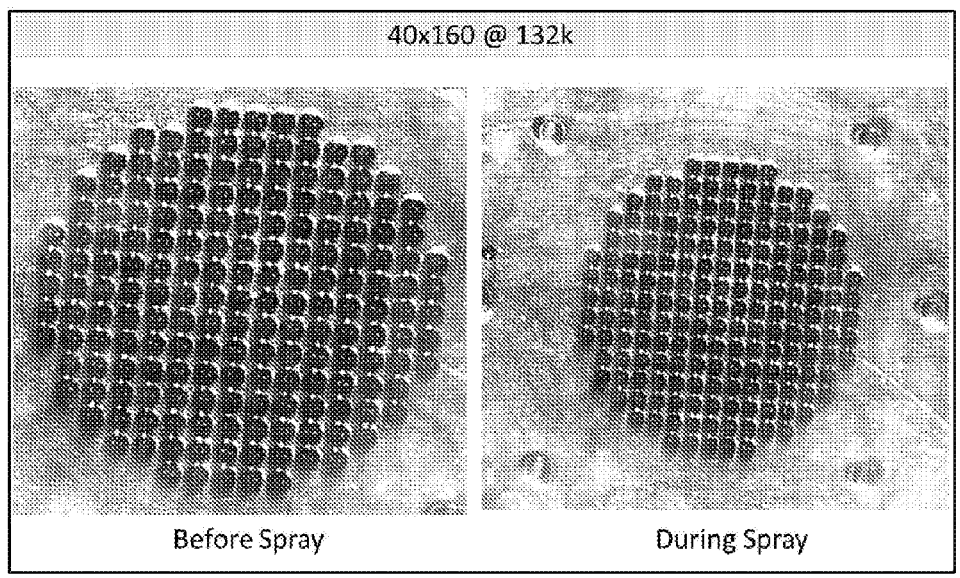
FIG. 9 illustrates another embodiment of a laminar NiCo ejector in operation according to the disclosure.

FIG. 7 describes the entrance length of developing flow as a function of Reynolds numbers which have been calculated for a velocity range of 1-10 m/s. As a result it was found that openings configured with entrance length, le, (i.e., channel length) exceeding 150 micrometers are better for creating laminar conditions for 40 micron exit diameters, while for 20 micron diameter holes, the entrance length le should exceed 100 microns. Thus, when constructing laminar ejector openings, the thickness (i.e., channel length) of a laminar ejector may be determined, at least in part, by the entrance diameter of the holes. In certain aspects, a sufficient channel length to achieve laminar flow of an ejected fluid by the time the fluid reaches the droplet ejection surface may be selected, as described herein.

FIGS. 8-11 are experimental results showing device performance to air intake during operation for ejectors having droplet generator plates with regular, non-laminar flow holes, as opposed to droplet generator plates with laminar flow holes. Droplet generator plates made from metal (NiCo, FIGS. 8 and 9) and polymer (PEEK, FIGS. 10 and 11) materials were considered. In the FIG. 8 embodiment the actuator was operated at 107 kHz and the droplet generator plate was provided with non-laminar flow holes. In the FIG. 9 embodiment the actuator was operated at 132 kHz and the droplet generator plate was provided with laminar flow holes.

Figure 10:
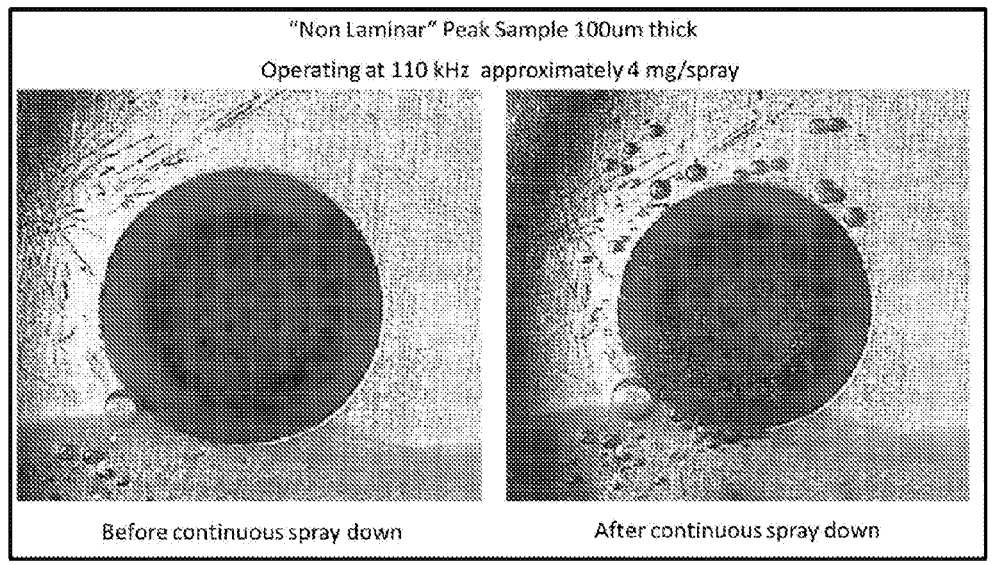
FIG. 10 illustrates one embodiment of a non-laminar PEEK ejector in operation according to the disclosure.
Figure 11:
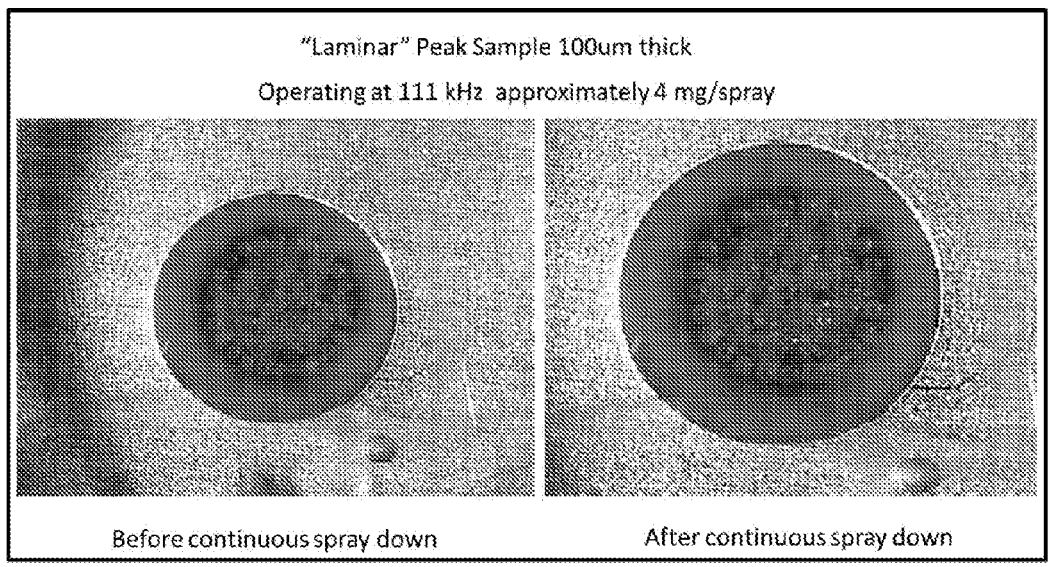
FIG. 11 illustrates another embodiment of a laminar PEEK ejector in operation, according to the disclosure.

In the embodiment of FIG. 10, a droplet generator plate thickness of 100 μm was used and the actuator was operated at 110 kHz. As in the FIG. 8 embodiment, the holes in the droplet generator plate were regular non-laminar flow holes. In the FIG. 11 embodiment, a droplet generator plate thickness of 100 μm was used and the actuator was operated at 111 kHz. As in the FIG. 9 embodiment, this droplet generator plate was provided with laminar flow holes. Thus for each material there is an example of the performance of a non-laminar and laminar ejector design constructed using the criterion described herein. The experiment was performed by mounting the device with a translucent reservoir filled with water (water has a high surface tension as shown in the Table 1, which aids in the formation of air bubbles providing a worst case scenario for the test) and open to the atmosphere. The back of the reservoir was imaged during peak spray conditions to track the formation of air bubbles into the system. The mounting conditions are the same for all compared samples. It was found that the laminar designed ejectors (FIGS. 9 and 11) performed better than the non-laminar ejectors (FIGS. 8 and 10) for all test. The laminar flow ejector design reduces the chance of outside air from entering the system during operation by removing air gaps within the ejector openings (nozzles) by keeping them filled with fluid during spray.

The benefits from screening the system from additional air intake include continued operation of the device without failure occurring from excess air in the system, which causes unpredictable changes of pressure within the system. The excess air can also contaminate the fluid within the system, which is undesirable when delivering pharmaceutical compositions, particularly low preservative and preservative free pharmaceutical compositions.

Figure 12:
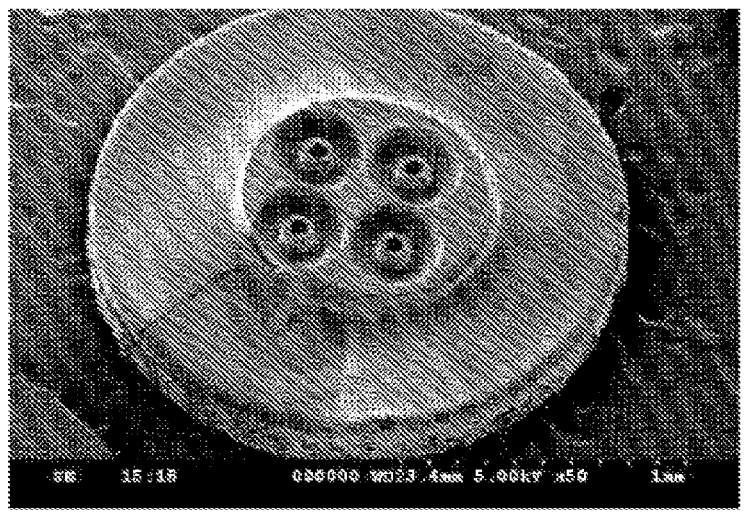
FIGS. 12-14 show three-dimensional views of ejector surfaces of different embodiments of droplet generator plates.
Figure 13:
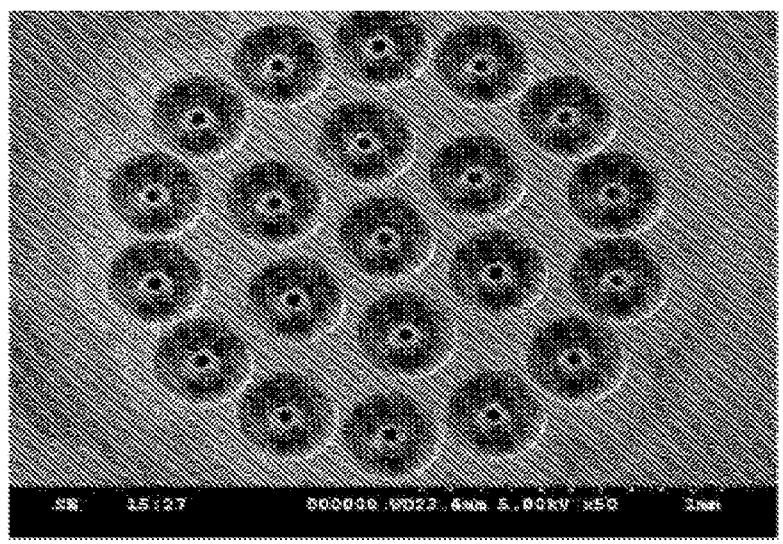
Figure 14:
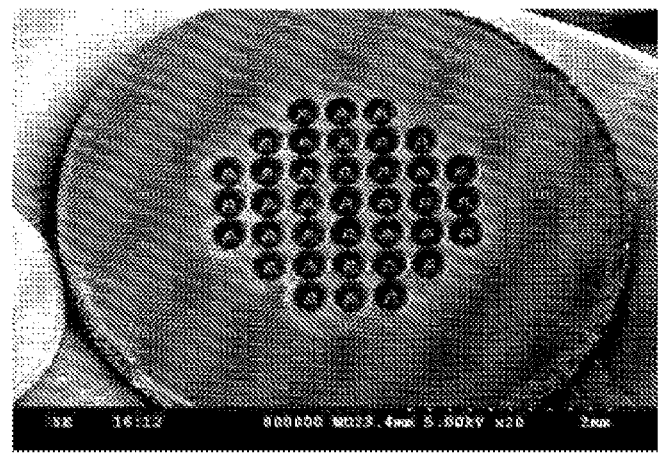

In additional aspects, in order to avoid build-up of liquid on the ejection surface of the droplet generator plate, the ejection surface may also be configured to define trenches around at least a portion of one or more ejector hole(s) as shown in FIGS. 12-14. The trenches may generally allow any fluid that may remain on the ejection surface to pool in the trenches, rather than blocking the ejection holes. This can further reduce build-up of fluid on the ejection surface and interference with droplet ejection.

To further counteract the effects of fluid beading on the ejection surface and the build-up of fluid, certain aspects further relate to the use of coatings on the surface of the ejector plate, e.g., gold coatings, silver coating, antimicrobial coatings, etc. In certain embodiments, coatings, e.g., gold coatings may be deposited on a generator plate, e.g., a PEEK generator plate to modify the surface (higher surface energy to increase he hydrophilicity) so that fluids flow more easily, to reduce fluid beading on the surface, etc.

Figure 15:
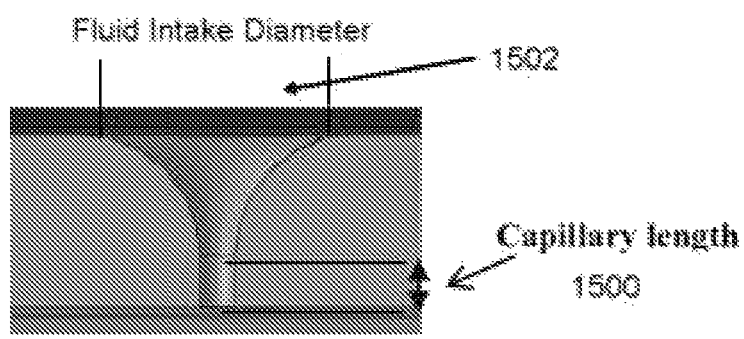
FIG. 15 shows a side view of a droplet generator plate hole according to the disclosure.

In yet other aspects, the thickness of the droplet generator plate may also affect laminar flow parameters, with better laminar flow being obtained from thicker plates with longer capillary tube length, while also affecting the oscillation of the plate, with thinner plates displaying better fluid ejection at higher frequencies. One embodiment was found to work well with a capillary tube length of 125 μm. The capillary tube or channel 1500 in relation to the flute intake 1502 for laminar flow is shown in FIG. 15.

Figure 16:
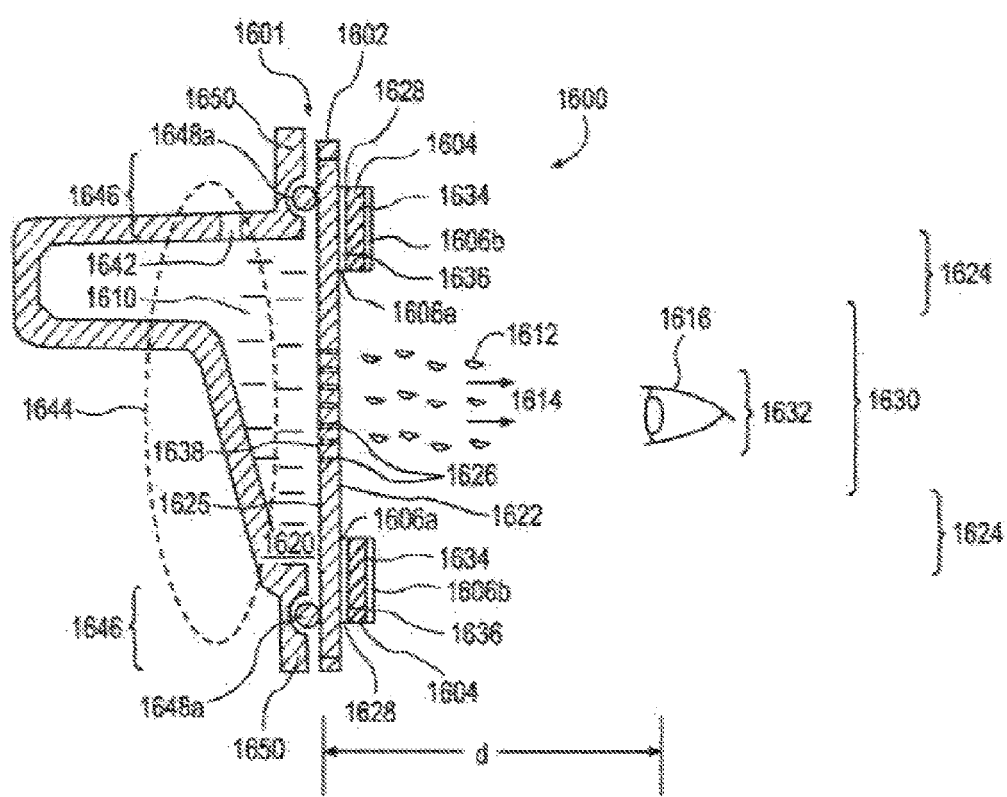
FIG. 16 shows a cross-sectional view of an ejector device, in accordance with aspects of the disclosure.

The ejector assembly, which may include an ejector plate coupled to a droplet generator plate and a piezo actuator. FIG. 16, for example, shows one embodiment of an ejector assembly 1600 that includes an ejector mechanism 1601 and reservoir 1620. The ejector mechanism 1601 may include an oscillating plate mechanism or system with ejector plate 1602 coupled to a generator plate or eliminating the generator plate and simply defining a central droplet generator region or ejector region 1632 that includes one or more openings 1626, which can be activated by (e.g. piezoelectric) actuator 1604. For ease of reference the droplet generator region 1632, whether it is integrally formed with the ejector plate or coupled to the ejector plate as a separate droplet generator plate, will be referred to interchangeably herein as a droplet generator plate or droplet generator region. Actuator 1604 vibrates or otherwise displaces ejector plate 1602 to deliver fluid 1610 from reservoir 1620, either as single droplet 1612 (droplet on demand) from one or more openings 1626, or as stream of droplets 1612 ejected from one or more openings 1626, along direction 1614.

In some applications, ophthalmic fluid may be ejected toward an eye 1616, for example in a human adult or child, or an animal. The fluid may contain a pharmaceutical agent to treat a discomfort, condition, or disease of the human or an animal, either in the eye or on a skin surface, or in a nasal or pulmonary application.

The attachment of ejector 1604 to ejector plate 1602 may also affect operation of ejection assembly 1600, and the creation of single droplets or streams thereof. In the implementation of FIG. 16, for example, ejector 1604 (or a number of individual ejector components 1604) may be coupled to a peripheral region of ejector plate 1602, on surface 1622 opposite reservoir 1620.

Central region 1630 of ejector plate 1602 includes droplet generator region 1632 with one or more openings 1626, through which fluid 1610 passes to form droplets 1612. Ejection region (or droplet generator) 1632 may occupy a portion of central region 1630, for example the center, or the ejection hole pattern of droplet generator region 1632 may occupy substantially the entire area of central region 1630. Further, open region 1638 of reservoir housing 1608 may correspond substantially to the size of ejection region 1632, or open region 1638 may be larger than ejection region 1632.

In this regard, the location of the openings may affect mass deposition, with ejection hole patterns near the center of central region 1630 generally being preferred. Further, the configuration and location of the piezoelectric actuator 1604 may impact operation, including the inner and outer diameters of the ejector plate 1602, and the thickness of the actuator 1604. In one embodiment a 19 mm outer diameter, 14 mm inner diameter, 250 microns thick actuator may be used in a non-edge mounted application.

As shown in FIG. 16, ejector plate 1602 is disposed over or in fluid communication with reservoir 1620, containing fluid 1610. For example, reservoir housing 1608 can be coupled to ejector plate 1602 at a peripheral region 1646 of the first major surface 1625, using a suitable seal or coupling such as O-rings 1648a to seal against reservoir wall 1650. A portion 1644 of reservoir housing 1608 may also be provided in the form of a collapsible bladder. However, the disclosure is not so limited, and any suitable bladder or reservoir may be used.

Figure 17A:
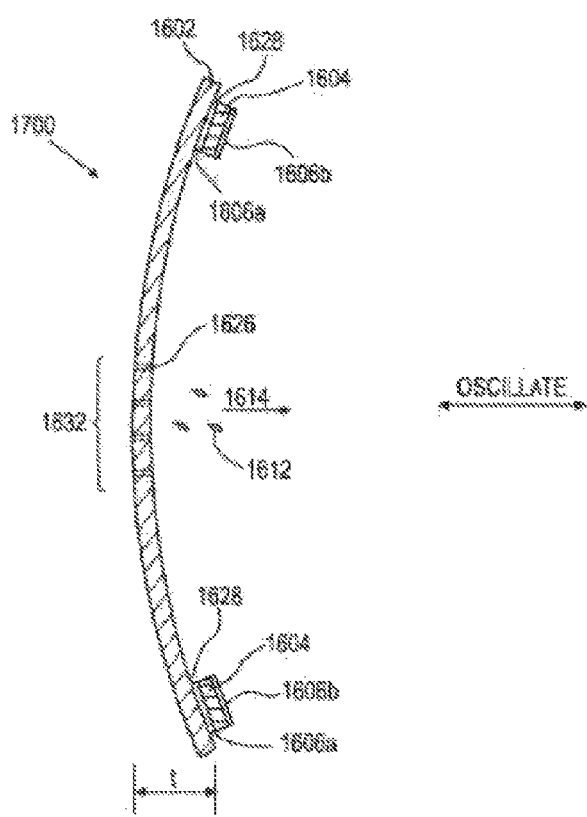
FIGS. 17A and B show cross-sectional views of an activated ejector plate for the ejector device of FIG. 16.
Figure 17B:
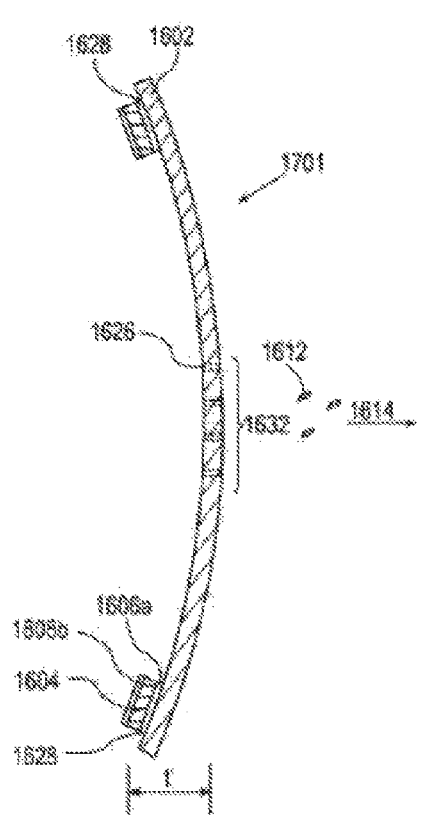

Prior to excitation, ejector assembly 1600 is configured in a resting state. When a voltage is applied across electrodes 1606a and 1606b on opposite surfaces 1634 and 1636 of (e.g., piezoelectric) actuator 1604, ejector plate 1602 deflects to change between relatively more concave shape 1700 and relatively more convex shape 1701, as shown in FIGS. 17A and 17B, respectively.

When driven with an alternating voltage, actuator 1604 operates to reverse the convex and concave shapes 1700 and 1701 of ejector plate 1602, inducing periodic movement (oscillation) of ejector plate 1602 in ejection region (droplet generator) 1632. Droplets 1612 are formed at apertures or openings 1626, as described above, with the oscillatory motion of ejection region 1632 causing one or more droplets 1612 to be ejected along fluid delivery (ejection) direction 1614, for example in a single-droplet (droplet on demand) application, or as a stream of droplets.

The drive voltage and frequency may be selected for improved performance of the ejection mechanism, as described above. In certain embodiments the oscillation frequency of actuator 1604 may be selected at or near a resonance frequency of the fluid filled ejector mechanism, or at one or more frequencies selected to oscillate ejector plate 1602 at such a resonance via superposition, interference, or resonant coupling.

When operated at or near a resonant frequency (for example, within the full width at half maximum of a resonance), ejector plate 1602 may amplify the displacement of ejector region (droplet generator) 1632, decreasing the relative power requirements of the actuator, as compared to a direct-coupling design. The damping factor of the resonance system, including ejector plate 1602 and droplet generator 1632, may also be selected to be greater than the piezoelectric actuator input power, in order to reduce fatigue and increase service life without substantial failure.

Figure 18:
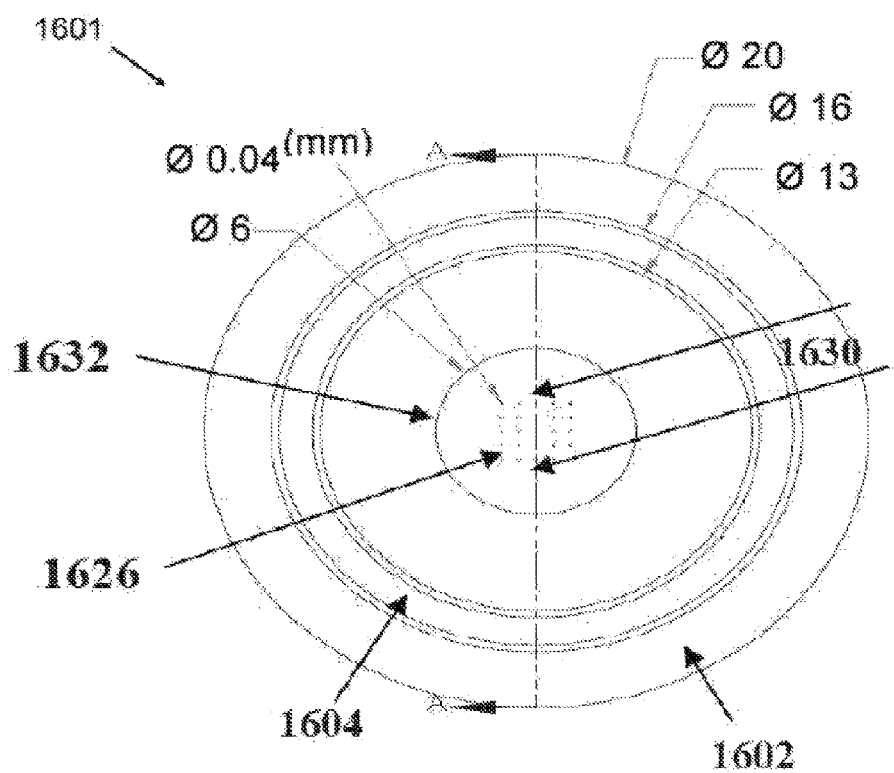
FIG. 18 is plan view of one embodiment of an ejector mechanism of the disclosure.

Examples of ejector assemblies are illustrated in U.S. Provisional Patent Application No. 61/569,739, "Ejector Mechanism, Ejector Device, and Methods of Use," filed Dec. 12, 2011, as incorporated by reference herein. In one particular embodiment, ejector plate mechanism 1601 may include a rotationally symmetric ejector plate 1602 coupled to a generator plate-type actuator 1604, for example as shown in FIG. 18, and as described in U.S. Provisional Patent Application No. 61/636,565, "Centro-Symmetric Lead Free Ejector Mechanism, Ejector Device, and Methods of Use," filed Apr. 20, 2012, also incorporated by reference herein. However, the disclosure is not so limited.

In the particular configuration of FIG. 18, generator plate-type actuator 1604 incorporates one or more individual piezoelectric devices or other actuator elements, as described above, for driving rotationally symmetric ejector plate 1602. Droplet generator plate 1632 includes a pattern of openings 1626 in center region 1630, and is driven via the ejector plate 1602 using a suitable drive signal generator circuit as described below. Exemplary techniques for generating drive voltages are illustrated in U.S. Provisional Patent Application No. 61/647,359, "Methods, Drivers and Circuits for Ejector Devices and Systems," filed May 15, 2012, as incorporated by reference herein.

Figure 19:
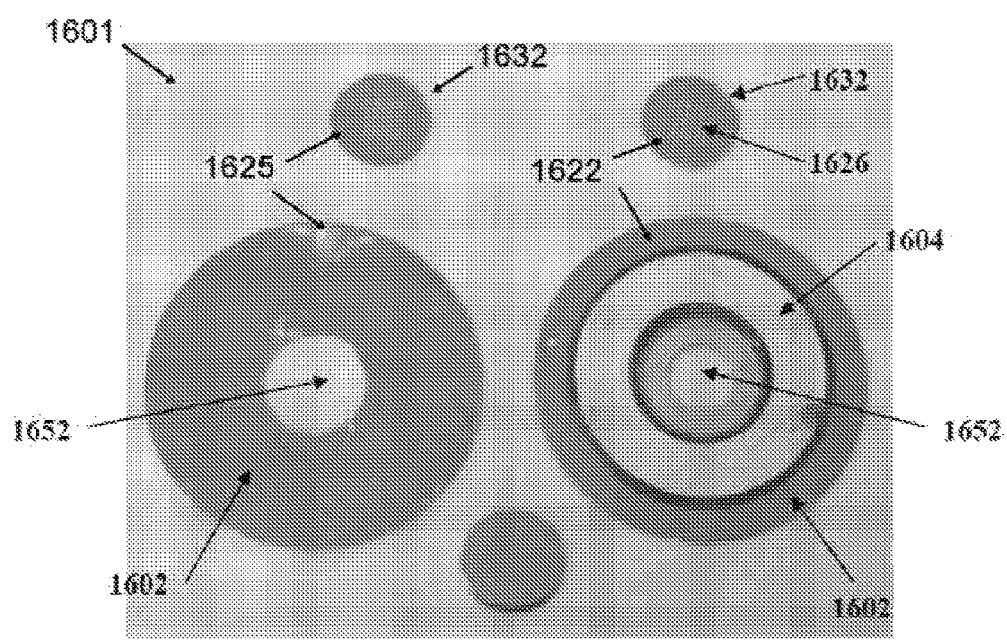
FIG. 19 is a dismantled view of an symmetric ejector mechanism of the disclosure.

FIG. 19 is a dismantled view of symmetric ejector mechanism 1601. In this embodiment, ejector plate 1602 utilizes a discrete (separate) droplet generator plate 1632, as shown on the left and right of FIG. 19 from the back (face down) surface 1625 and the front (face up) surface 1622, respectively. Droplet generator plate 1632 is mechanically coupled to ejector plate 1602 in central aperture 1652, and includes a pattern of openings 1626 configured to generate a stream of fluid droplets when driven by generator-plate type actuator 1604, as described above.

Figure 20:
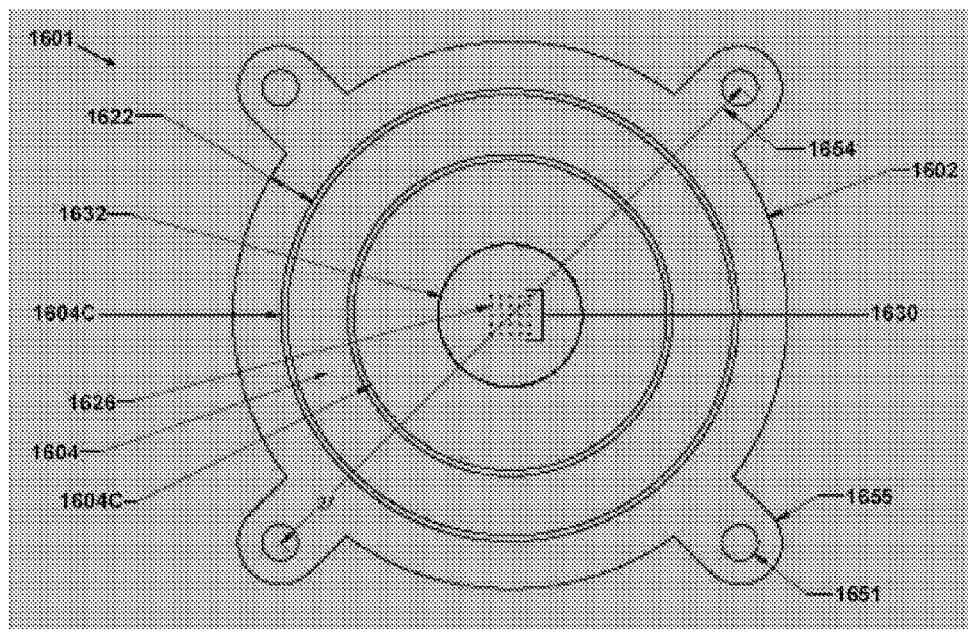
FIG. 20 is a plan view of a symmetric ejector mechanism of the disclosure.

FIG. 20 is a plan view of symmetric ejector mechanism 1601. Ejector mechanism 1601 includes ejector plate 1602 with mechanical couplings 1604C to generator plate-type actuator 1604 and droplet generator plate 1632 with a pattern of openings 1626 in central region 1630, as described above. Ejector mechanism 1601 may be coupled to a fluid reservoir or other ejection device component via apertures 1651 in tab-type mechanical coupling elements 1655, or using another suitable connection as described above with respect to FIG. 16.

As shown in FIG. 20, ejector mechanism 1601 and ejector plate 1602 may be defined by overall dimension 1654, for example about 21 mm, or in a range of about 10 mm or less to about 25 mm or more, depending upon application. Suitable materials for ejector plate 1602 and drop generator 1632 include, but are not limited to, flexible stress and fatigue-resistant metals such as stainless steel.

For orientation purposes, the different elements of ejector mechanism 1601 as shown in FIGS. 18-20 may be described relative to the location of fluid 1610 or reservoir 1620, as described above with respect to FIG. 16. In general, the proximal elements of mechanism 1601 are located closer to fluid reservoir 1620 and the distal elements are located farther from fluid reservoir 1620, as defined along the droplet stream or ejection direction 1614.

The ejector assembly described herein may be incorporated into an ejector device. Exemplary ejector devices are illustrated in U.S. patent application Ser. No. 13/184,484, filed Jul. 15, 2011, the contents of which are herein incorporated by reference.

Many implementations of the invention have been disclosed. This disclosure contemplates combining any of the features of one implementation with the features of one or more of the other implementations. For example, any of the ejector mechanisms, or reservoirs can be used in combination with any of the disclosed housings or housing features, e.g., covers, supports, rests, lights, seals and gaskets, fill mechanisms, or alignment mechanisms. Further variations of any of the elements of any of the embodiments herein are within the scope of ordinary skill and are contemplated by this disclosure. Such variations include selection of materials, coatings, or methods of manufacturing. Any of the electrical and electronic technology can be used with any of the implementations without limitation. Furthermore, any networking, remote access, subject monitoring, e-health, data storage, data mining, or internet functionality with respect to data captured by the device, is applicable to any and all of the implementations and can be practiced therewith. Further still, additional diagnostic functions, such as performance of tests or measurements of physiological parameter may be incorporated into the functionality of any of the implementations. Performance of glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms than those described in the incorporated prior applications. For example, the device or base may be equipped with or coupled to an iris or retina scanner to create a unique id to match a device to the user, and to delineate between eyes. Alternatively, the device or base may be coupled to or include sophisticated imaging devices for any suitable type of photography or radiology.

Although the foregoing describes various embodiments by way of illustration and example, the skilled artisan will appreciate that various changes and modifications may be practiced within the spirit and scope of the present application.

What is claimed is:

1. A device for generating a directed stream of droplets, the device comprising:
a housing;

a reservoir disposed within the housing for receiving a volume of fluid; and an ejector mechanism in fluid communication with the reservoir and configured to generate the directed stream of droplets of said fluid, the ejector mechanism comprising a generator plate and a piezoelectric actuator;

wherein the generator plate includes a fluid facing surface, a droplet ejection surface, and a plurality of openings formed through its thickness between said surfaces;

wherein the piezoelectric actuator is operable to directly or indirectly oscillate the generator plate, at a frequency to generate the directed stream of droplets of said fluid; and wherein the plurality of openings of the generator plate have a gradual slope of change from the fluid facing surface to the droplet ejection surface so as to provide an external entry radius of curvature having a circular shape thereby reducing airflow through the plurality of openings from the droplet ejection surface to the fluid facing surface during generation of the directed stream of droplets to provide the fluid with laminar flow as it passes through the openings.

2. The device of claim 1, wherein the intake from the fluid facing surface into each of the openings defines a fluted intake providing a gradual transition from the fluid facing surface into the opening.

3. The device of claim 1, wherein at the droplet ejection surface trench is defined around at least one of the openings.

4. The device of claim 1, wherein the ratio of size of the radius of curvature to the size of the opening at the droplet ejection surface is: greater than about 2.5, when the opening at the droplet ejection surface is greater than about 40 μm, or the ratio is greater than about 5, when the opening at the droplet ejection surface is less than about 40 μm.

5. The device of claim 1, wherein each opening defines a fluted intake and a channel that extends to the droplet ejection surface, the channel being configured with sufficient length so as to achieve laminar flow of the fluid prior to the fluid reaching the ejection surface.

6. The device of claim 1, wherein said ejector mechanism further comprises an ejector plate coupled to the generator plate and the piezoelectric actuator, the piezoelectric actuator being operable to oscillate the ejector plate, and thereby the generator plate, at the frequency to generate the directed stream of droplets.

7. The device of claim 6, wherein the ejector plate has a central open region aligned with the generator plate, and the piezoelectric actuator is coupled to a peripheral region of the ejector plate so as not to obstruct the plurality of openings of the generator plate.

8. The device of claim 7, wherein the plurality of openings of the generator plate are disposed in a center region of the generator plate that is uncovered by the piezoelectric actuator and aligned with the central open region of the ejector plate.

9. The device of claim 7, wherein the generator plate has a reduced size relative to the ejector plate, and the size of the generator plate is determined, at least in part, by the area occupied by the center region and the arrangement of the plurality of openings.

10. The device of claim 1, wherein the ejector mechanism is configured to eject the directed stream of droplets such that at least about 75% of the mass of the ejected droplets deposit on the target.

11. The device of claim 1, wherein the ejector mechanism is configured to eject the directed stream of droplets having an average ejected droplet diameter in the range of 20 to 400 microns.

12. The device of claim 1, wherein the ejecting mechanism is configured to eject the directed stream of droplets having an average initial ejected velocity in the range of 0.5 m/s to 10 m/s.

* * * * *